(12) United States Patent
Kelly

(10) Patent No.: US 6,893,257 B2
(45) Date of Patent: May 17, 2005

(54) ORTHODONTIC APPLIANCE WITH PLACEMENT ENHANCEMENT STRUCTURE

(75) Inventor: John S. Kelly, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 165 days.

(21) Appl. No.: 10/324,655

(22) Filed: Dec. 19, 2002

(65) Prior Publication Data

US 2004/0121279 A1 Jun. 24, 2004

(51) Int. Cl.[7] .................................................. A61C 3/00
(52) U.S. Cl. ............................................. 433/9; 433/17
(58) Field of Search .......................... 433/8, 9, 10, 11, 433/12, 13, 14, 15, 16, 17, 23

(56) References Cited

U.S. PATENT DOCUMENTS

| | | | |
|---|---|---|---|
| 3,765,091 A | 10/1973 | Northcutt | |
| 3,964,165 A | 6/1976 | Stahl | |
| 4,219,617 A | 8/1980 | Wallshein | |
| 4,302,532 A | 11/1981 | Wallshein | |
| 4,531,911 A | 7/1985 | Creekmore | |
| D290,040 S | 5/1987 | Kelly | |
| 4,820,151 A | 4/1989 | Pospisil | |
| 4,936,773 A | 6/1990 | Kawaguchi | |
| D315,957 S | 4/1991 | Kelly et al. | |
| 5,059,119 A | 10/1991 | Snead | |
| 5,094,614 A | 3/1992 | Wildman | |
| 5,151,028 A | 9/1992 | Snead | |
| D331,975 S | 12/1992 | Pospisil | |
| 5,320,525 A | 6/1994 | Förster | |
| 5,328,363 A | * 7/1994 | Chester et al. ................ 433/9 |
| 5,380,196 A | 1/1995 | Kelly et al. | |
| 5,439,379 A | 8/1995 | Hansen | |
| 5,456,599 A | 10/1995 | Hanson | |
| 5,522,725 A | 6/1996 | Jordan et al. | |
| 5,556,277 A | 9/1996 | Yawata et al. | |
| 5,618,175 A | 4/1997 | Reher et al. | |
| 5,707,231 A | 1/1998 | Watt et al. | |
| 5,746,594 A | 5/1998 | Jordan et al. | |
| 5,820,371 A | 10/1998 | Förster | |
| 5,910,007 A | 6/1999 | Shimodaira et al. | |
| 5,911,574 A | 6/1999 | Casey | |
| 6,206,690 B1 | 3/2001 | Vargas | |
| 6,217,322 B1 | 4/2001 | Kesling | |
| 6,241,516 B1 | 6/2001 | Orikasa et al. | |
| 6,280,185 B1 | 8/2001 | Palmer et al. | |
| 6,709,268 B2 * | 3/2004 | Pospisil et al. ................ 433/17 |

FOREIGN PATENT DOCUMENTS

| | | |
|---|---|---|
| DE | 19856794 | 6/2000 |
| EP | 0624354 | 11/1994 |
| EP | 0976368 | 2/2000 |
| WO | WO 01/22901 | 4/2001 |

OTHER PUBLICATIONS

3M Unitek Product Catalog 2001–2002, pp. 3–1 to 3–17.
GAC Orthodontic Products, (1983), pp. A1, E1–E10.
GAC Orthodontic Catalog Copyright 1997, pp. 58–77.
Pending U.S. Appl. No. 10/324,265, filed Dec. 19, 2002 (58255US002).

* cited by examiner

Primary Examiner—Todd E. Manahan
(74) Attorney, Agent, or Firm—James D. Christoff

(57) ABSTRACT

An orthodontic appliance that is adapted for bonding directly to the enamel surface of a patient's tooth has structure for enhancing placement of the appliance on the tooth surface. The structure facilitates gripping the appliance by a hand instrument so that the appliance does not unduly shift or rock during a bonding procedure. In certain aspects of the invention, the placement enhancement structure comprises one or more protrusions located along sides of the appliance, and optionally some of the protrusions are located within a recess that extends along an occlusal or gingival side of the appliance.

18 Claims, 3 Drawing Sheets

ORTHODONTIC APPLIANCE WITH PLACEMENT ENHANCEMENT STRUCTURE

BACKGROUND OF THE INVENTION

1. Field of the Invention

This invention broadly relates to an appliance that is secured to a tooth during the course of orthodontic treatment. More particularly, the present invention is directed to an orthodontic appliance having structure that facilitates manipulation, placement and removal of the appliance by the orthodontic practitioner.

2. Description of the Related Art

Orthodontia is a specialized field within the general subject area of dentistry. Orthodontic treatment involves movement of malpositioned teeth to correct locations along the dental arch. Orthodontic treatment can result in improved occlusion for the patient as well as a more pleasing aesthetic appearance.

One type of orthodontic treatment involves the use of a set of components that are collectively known as "braces". In this type of treatment, small slotted devices known as brackets are secured to the patient's anterior, cuspid and bicuspid teeth. An archwire is received in the slots of the brackets and forms a track to guide movement of the teeth to desired positions.

Each end of an orthodontic archwire is often received in an enclosed elongated passageway of a small device known as buccal tube. Buccal tubes are connected to the patient's molar teeth. The enclosed passageway helps prevent the end of the archwire from contacting the patient's soft tissue in the oral cavity, which might otherwise lead to pain and injury. In some instances, buccal tubes are provided with a convertible cap along one side of the passageway that can be opened in order to convert the tube into a bracket when desired.

In the past, orthodontic brackets and buccal tubes were often welded to a metallic band that was adapted to encircle the patient's tooth. The band was selected to match the shape of the tooth in order to provide a secure connection between the tooth and the appliance. Typically, an adhesive known as band cement was placed along the inner circumference of the band in order to help avoid gaps between the band and the tooth surface. The cement also helped to preclude undue rocking of the band once the band was placed over the tooth.

Orthodontic bands are often manufactured with a shape that closely matches the expected shape of the patient's tooth. For example, the band may have one or more indentations that are adapted to be received between adjacent cusps of the molar tooth. Bands are usually not cylindrical but instead have somewhat flattened sides that are adapted to matingly fit against matching sides of a particular tooth.

When the practitioner places a selected band over the patient's tooth, the shape of the band (including any flattened regions and cusp indentations) helps to ensure that the band is properly positioned with respect to a rotative orientation about the longitudinal axis of the tooth. As a consequence, when the band is fully seated on the tooth, the band and the accompanying appliance are located in a proper, predefined orientation relative to the tooth. In many instances, the practitioner need only place the band in a rotative position that is approximate to the final desired position, since the band will often shift somewhat in rotative directions to accommodate the shape of the tooth as it slides across the tooth surface and moves toward its final desired position.

However, orthodontic bands are highly visible, especially when placed over the patient's front teeth that are near the mouth. Consequently, bands are not considered aesthetic. Bands can serve as a source of embarrassment to the patient, particularly among adolescent patients who may experience teasing from classmates. In addition, the steps of selecting the proper band and welding the selected band to the desired appliance result in an expense of time and money that is best avoided if at all possible.

As a result, there has been increased interest in recent years in the use of orthodontic appliances that are directly bonded to the surface of the tooth with an adhesive. Such appliances avoid the need for selecting a properly sized band and welding the appliance to the band at a certain, predefined location. Moreover, such appliances are considered more aesthetic in use because the lack of the band renders the appliance more difficult to see.

However, appliances that are directly bonded to the tooth surface, also are known as "direct bond" appliances, are generally considered to require careful attention by the practitioner when attempting to place the appliance to the tooth. According to certain types of treatment techniques, direct bond appliances should be positioned at certain, predefined locations on the tooth so that the tooth is properly oriented with respect to the remaining teeth at the conclusion of treatment. Placement of appliances at correct locations on the tooth is especially crucial when the practitioner is using the "Straight Edge" technique, a technique that aims to result in a straight and level archwire at the conclusion of treatment.

An orthodontic appliance that is improperly placed on the tooth surface may cause unsatisfactory treatment results. For example, if the appliance is bonded to the tooth at a location that is offset from its intended location, the resulting orientation of the tooth at the conclusion of treatment may be offset a corresponding distance if the practitioner is using the "Straight Edge" technique. As a consequence, precise manipulation of the appliance is often needed during the bonding procedure in order to ensure that the resulting placement of the appliance on the tooth is exactly as intended.

In addition, it is also important to ensure that the direct bond appliance is firmly embedded in adhesive during the bonding procedure. Conventionally, a layer of adhesive is placed on the base of the appliance and the appliance is then maneuvered into position over the tooth surface. The practitioner then presses the base of the appliance against the tooth, preferably with sufficient force to extrude a portion of the adhesive from the sides of the base. Such practice helps to ensure that there are no gaps or voids between the base of the appliance and the tooth, which might otherwise trap food and contribute to caries.

As such, manipulation of direct bond appliances during a bonding procedure is an important task, and mistakes are best avoided. Oftentimes, the practitioner will use a hand instrument such as fine-tipped pliers to hold the appliance and manipulate the appliance during the bonding procedure. However, orthodontic appliances are relatively small and visibility within the oral cavity is limited, especially in posterior regions next to the molar teeth. Maneuvering the appliance within the confines of the oral cavity is also troublesome.

Moreover, certain types of orthodontic adhesives exhibit characteristics that lend difficultly to the bonding procedure. For example, some types of orthodontic adhesives, known as "chemical cure" adhesives, begin a curing reaction as soon as two components of the adhesive are mixed together. Once the curing reaction begins, the practitioner must complete the bonding procedure before the adhesive has hardened. As a result, practitioners using chemical cure adhesives must work steadily and accurately to complete the bonding procedures within a certain period of time.

Although the orthodontic appliances that are currently available are considered generally satisfactory by many practitioners, there is a continuing need to improve the state of the art, particularly with respect to the placement and bonding of direct bond appliances. Preferably, such improvements would not only facilitate the practitioner's tasks but also help improve the results evidenced by the patient's dentition at the conclusion of treatment.

SUMMARY OF THE INVENTION

The present invention is directed to an orthodontic appliance having structure for enhancing the maneuverability of the appliance by the practitioner. The structure is useful during a bonding procedure, such as when the appliance must be carefully moved to a precise, pre-selected location on the surface of the tooth. The structure is also useful for shifting the appliance as may be needed during a bonding procedure to firmly embed the base of the appliance in the adhesive. Additionally, the structure is useful for grasping the appliance at the conclusion of treatment when it is desired to detach the appliance from the tooth surface.

The placement enhancement structure of the orthodontic appliances of the present invention may take any one of several forms. For example, the placement enhancement structure may comprise one or more protrusions located along sides of the appliance. Examples of suitable protrusions include ridges, bumps, and posts. Optionally, the protrusions may be provided within a recess that is located along a top or bottom side of the appliance.

The placement enhancement structure of the orthodontic appliance according to the invention facilitates a secure connection to a hand instrument such as a pair of fine-tipped pliers or other tool that is used to grasp and manipulate the appliance. The placement enhancement structure helps to avoid slippage between the appliance and the hand instrument during a bonding procedure so that the relative orientation of the appliance relative to the hand instrument does not unduly shift. Such structure helps to ensure that the resulting position of the appliance on the tooth closely matches the preselected, desired position.

In more detail, the present invention in one aspect relates to an orthodontic appliance that comprises a base for bonding the appliance to a tooth and a body extending outwardly from the base. The body has an occlusal side (i.e., a side facing the outer tips of the tooth) and a gingival side (i.e., a side facing the patient's gums or gingiva). The appliance also includes an elongated archwire slot that extends across the body in a generally mesial-distal direction (i.e., in directions toward and away from the middle of the patient's dental arch, following along the path of the arch). The orthodontic appliance also includes placement enhancement structure extending along at least one of the occlusal and gingival sides for facilitating gripping of the appliance.

The present invention is also directed in another aspect to an orthodontic appliance that comprises a base for bonding the appliance to a tooth and a body extending outwardly from the base. The body has an occlusal side and a gingival side. An elongated archwire slot extends across the body in a generally mesial-distal direction. The appliance includes at least one recess extending along at least one of the occlusal and gingival sides. The appliance also includes placement enhancement structure located in at least one recess for facilitating gripping of the appliance.

These and other aspects are described in more detail below and are illustrated in the accompanying drawings.

DETAILED DESCRIPTION OF THE PREFERRED EMBODIMENTS

Figure 1:
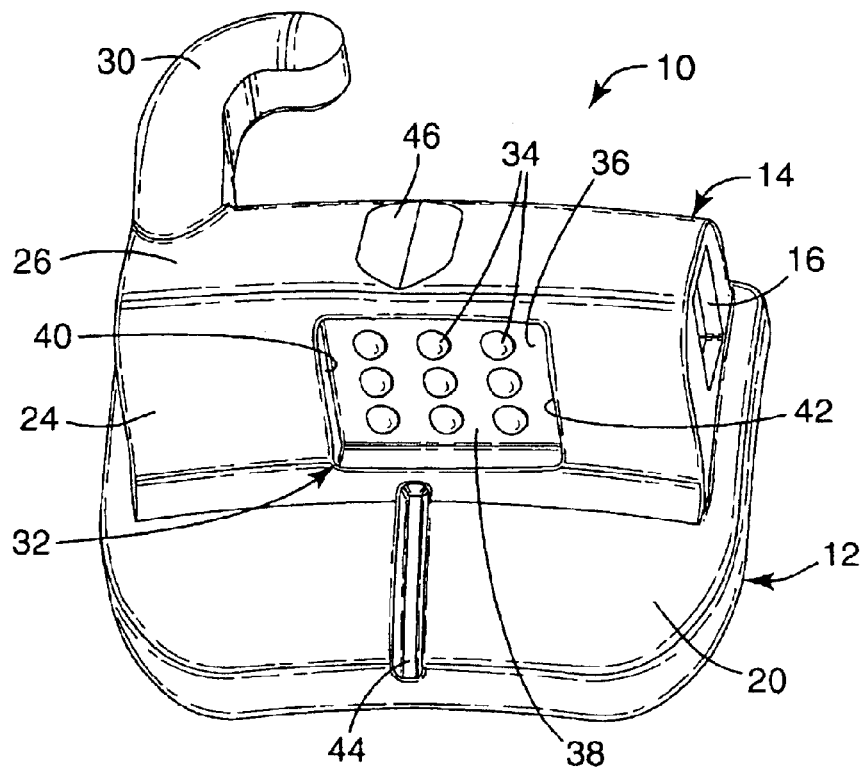
FIG. 1 is a perspective view of an orthodontic appliance constructed in accordance with one embodiment of the invention, looking at the appliance in a direction toward its occlusal, distal and buccolabial sides.
Figure 2:
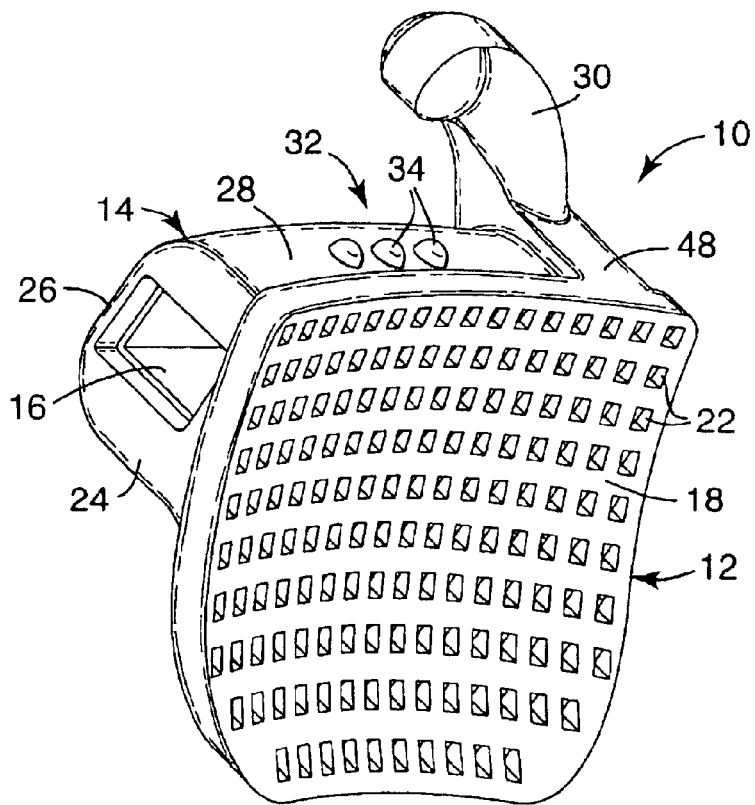
FIG. 2 is a perspective view of the appliance shown in FIG. 1 but looking at the appliance in a direction toward its gingival, distal and lingual sides.

An orthodontic appliance according to one embodiment of the present invention is illustrated in FIGS. 1 and 2 and is broadly designated by the numeral 10. The appliance 10 includes a base 12 and a body 14 that is connected to the base 12. An elongated archwire slot 16 extends through the body 14 in a generally mesial-distal direction for receiving an archwire.

In more detail, the base 12 includes a first, tooth-facing side 18 that is illustrated in FIG. 2 and a second side 20 that is opposite to the first side 18. The second side 20 is shown in FIG. 1. In the illustrated example, the appliance 10 is adapted to be secured to a buccolabial side of a tooth (i.e., a side of the tooth facing the patient's cheeks or lips). Consequently, the first side 18 of the base 12 in this example can also be deemed a lingual side and the second side 20 can also be deemed a buccolabial side.

As shown in FIG. 2, the first side 18 of the base 12 is provided with a series of cavities 22 for receiving a portion of an orthodontic adhesive that is used to affix the appliance 10 to the enamel of a patient's tooth. In this embodiment, the cavities 22 are arranged in a rectangular array and have a square configuration when viewed in a buccolabial direction. However, other arrays and shapes are also possible. Alternative cavities as well as other features of the appliance are described in applicant's co-pending U.S. patent application entitled "LOW PROFILE ORTHODONTIC APPLIANCE", Ser. No. 10/324,265, filed on even date herewith and expressly incorporated by reference herein.

Preferably, the first side 18 of the base 12 has a shape that matches the configuration of the tooth surface for which the appliance 10 is intended. In the example shown in the drawings, the first side 18 has a concave, compound contour that is adapted to mate with the convex shape of a molar tooth. One of the curves can be viewed in a reference plane parallel to the occlusal plane of the patient when the appliance 10 is mounted on a tooth. The remaining curve can be viewed in a reference plane perpendicular to the occlusal plane. However, in certain instances (such as in appliances intended for anterior teeth), the base may be curved in only one direction or alternatively have a flat configuration.

The body 14 in this embodiment is a rectangular "U"-shaped member having three sides: an occlusal side 24 (see FIG. 1), a buccolabial side 26 and a gingival side 28 (see FIG. 2). The archwire slot 16 extends in a longitudinal direction through the body 14 and has a generally rectangular configuration when considered in reference planes perpendicular to the longitudinal axis of the archwire slot 16. A lingual edge of the occlusal side 24 and a lingual edge of the gingival side 28 are integrally connected directly to the second side 20 of the base 12.

Optionally, and as shown in the drawings, the appliance 10 includes a gingival hook 30 that is connected to a mesial end section of the body 14. The hook 30 has a somewhat "L"-shaped configuration and is connected to an area of the body 14 that is near an intersection of the buccolabial side 26 and the gingival side 28. The hook 30 is useful as a coupling for connection to a force module or other component as may be desired by the practitioner during the course of treatment.

As shown in FIG. 2, the appliance 10 includes an enlarged section 48 that is adjacent the mesial end of the archwire slot 16. The enlarged section 48 extends from the gingival hook 30 in a lingual direction toward the base 12. The enlarged section 48 enables the mesial end of the archwire slot 16 to include a chamfered region to facilitate insertion of an archwire.

The appliance 10 also includes placement enhancement structure 32 for facilitating gripping of the body 14. The placement enhancement structure 32 in this example comrises two arrays of protrusions 34. A first array of protrusions 34 is located on the occlusal side 24 of the body 14 and can be observed in FIG. 1. The second array of protrusions 34 is located on the gingival side 28 of the body 14 and is depicted in FIG. 2.

In the illustrated embodiment, the protrusions 34 are rounded, semi-spherical bumps. However, a variety of other shapes are also possible. For example, the protrusions 34 may comprise pins, posts, pyramids, truncated pyramids, cones, truncated cones and the like. The protrusions 34 may also be elongated ridges, such as rectangular, square or rounded bars.

Other types of placement enhancement structures are also possible. For example, the structure 32 may comprise a series of holes, pores or cavities. The cavities may be discreet and spaced apart from each other, or interconnected with each other. Optionally, the cavities may be elongated, such as troughs or channels.

Figure 5:
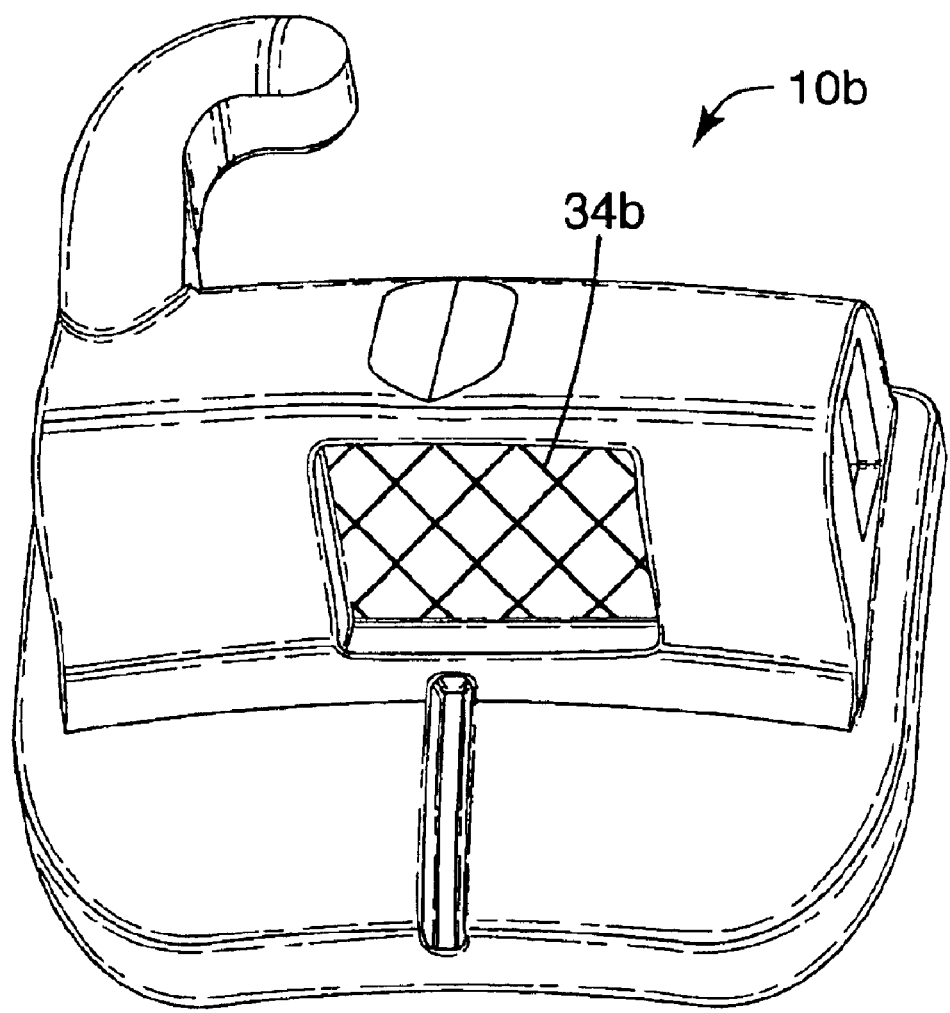
FIG. 5 is a view somewhat similar to FIG. 1 but showing the appliance with cross-hatching.

As an additional option, the placement enhancement structure 32 may comprise a roughened surface, a knurled surface, or a surface that is provided with other types of patterns and/or cross-hatchings. An exemplary cross-hatching 34b is illustrated in FIG. 5 for an appliance 10b. Optionally, the placement enhancement structure 32 may comprise any combination of the foregoing. The structure 32 may also be sandblasted or etched by a laser to further enhance grasping by a hand instrument. Preferably, the placement enhancement structure 32 has an average surface roughness ("$R_a$") greater than about 250 microinch, and more preferably greater than about 500 microinch.

The array of protrusions 34 located on the gingival side 28 of the appliance 10 comprises a single row of three bumps, while the array of protrusions 34 on the occlusal side 24 of the appliance 10 comprises three rows of three bumps. In addition, one or more of the placement enhancement structures 32 is located in a recess of the body 14. In the illustrated embodiment, the protrusions 34 that are located on the occlusal side 24 of the body 14 are located in a recess 36 of the occlusal side 24.

The recess 36 includes a bottom wall section 38 that is preferably generally parallel to the occlusal plane of the patient when the appliance 10 is mounted on the patient's tooth. The protrusions 34 in the recess 36 extend outwardly in an occlusal direction from the wall section 38. The wall section 38 is located in a gingival direction relative to the exterior occlusal surface of the occlusal side 24.

The recess 36 also includes a mesial wall section 40 and a distal wall section 42 spaced from the mesial wall section 40. The wall sections 40, 42 represent the mesial and distal extremities, respectively, of the recess 36. Optionally, the wall sections 40, 42 extend in reference planes that are generally perpendicular to the longitudinal axis of the archwire slot 16.

The placement enhancement structure 32 facilitates gripping of the appliance 10 by a hand instrument such as fine-tipped pliers or other tool used by the practitioner to grasp the body 14. The placement enhancement structure 32 helps ensure that the appliance 10 will not unduly shift relative to the hand instrument when the practitioner is maneuvering the appliance 10 in the oral cavity. Optionally, the tips of the hand instrument are also roughened or have protrusions. As an additional option, the protrusions 34 may be received in matching recesses located in the tips of the hand-instrument to provide a snug, interlocking relation.

During a bonding procedure, the practitioner may press the base 12 against the tooth surface with force in order to firmly embed the first side 18 of the base 12 in the adhesive. The placement enhancement structure 32 reduces the likelihood that the appliance 10 will shift or rock relative to the hand instrument, so that all four edges of the base 12 are embedded in the adhesive in relatively close proximity to the tooth surface and preferably at an equal distance from the same. This aspect is especially important when bonding the appliance 10 to teeth that are located in posterior regions of the oral cavity, such as the patient's molar teeth. The posterior regions are considered difficult to access and visibility of the bonding procedure is somewhat limited.

The provision of the protrusions 34 in the recess 36 also provides important advantages for the practitioner. For example, the mesial and distal wall sections 40, 42 provide a barrier for lateral movement of the tips of the hand instrument, and help ensure that the tips do not excessively shift in a mesial or distal direction away from the center of the appliance 10. As a consequence, the tips of the hand instrument remain firmly seated on the protrusions 34.

Advantageously, the recess 36 provides a lowered mounting surface for the protrusions 34 so that the protrusions 34 do not unduly extend past the occlusal side 24. As a result, the exterior surface of the body 14 might be deemed smoother than would be otherwise possible. Moreover, when certain tumbling media is used in the manufacturing process for smoothing the appliance 10, the provision of the recess 36 reduces contact of the tumbling media with the protrusions 34 so that the protrusions 34 are not significantly exposed to the tumbling media and unduly smoothed.

Optionally, and as shown in FIG. 1, the appliance 10 includes an alignment mark 44 that extends across the second side 20 of the base 12 in a generally occlusal-gingival direction. The alignment mark 44 is useful for positioning the appliance 10 on the surface of the tooth. For example, the practitioner may elect to align the alignment mark 44 with the long axis of the tooth so that the archwire slot 16 is in a certain, predefined orientation relative to the tooth and to other orthodontic components in the oral cavity.

As an additional option, the appliance 10 may include a positioning notch 46 that is also shown in FIG. 1. The notch 46 in this example is placed on the buccolabial side 26 of the body 14 and can be used during a bonding procedure for shifting the appliance 10 to a precise location. For example, once the base 12 of the appliance 10 has been firmly embedded in the adhesive, the practitioner may elect to place the tip of a probe in the notch 46 and shift the appliance 10 slightly until a desired position is attained.

The appliance 10 may be made of any material that is suitable for use in the oral cavity and has sufficient strength to resist the stresses normally encountered during the course of orthodontic treatment. Examples of such materials include metallic materials including alloys of stainless steel and titanium. Ceramic materials may also be employed, such as translucent polycrystalline alumina. A particularly preferred appliance is made of stainless steel series 17-4PH or 316L using a metal injection molding technique.

Figure 3:
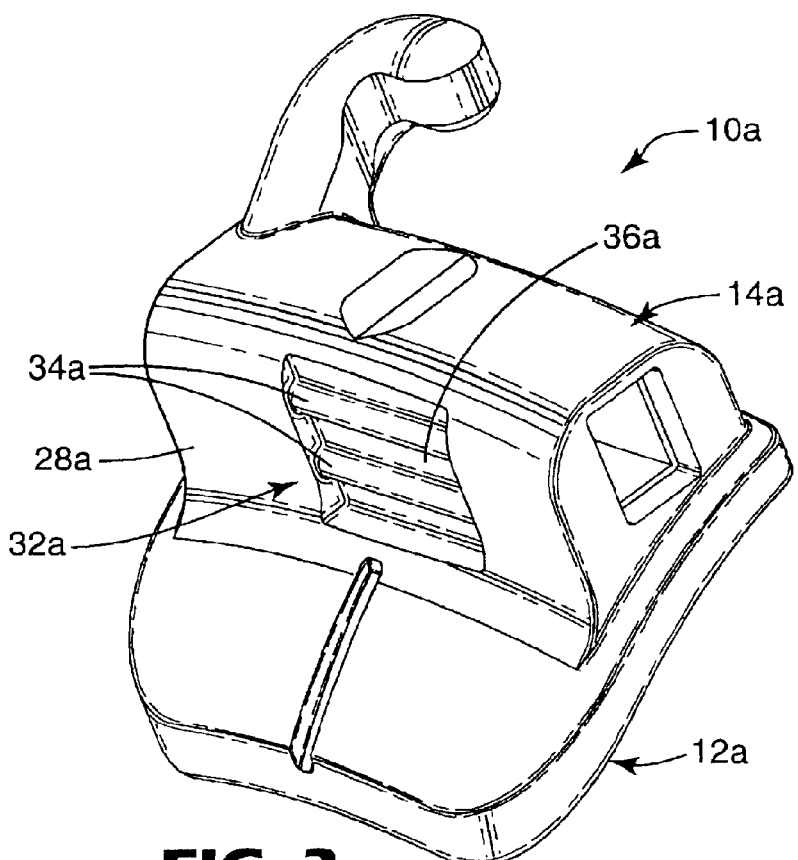
FIG. 3 is a perspective view of an orthodontic appliance in accordance with another embodiment of the invention, looking at the appliance toward its occlusal, mesial and buccolabial sides.
Figure 4:
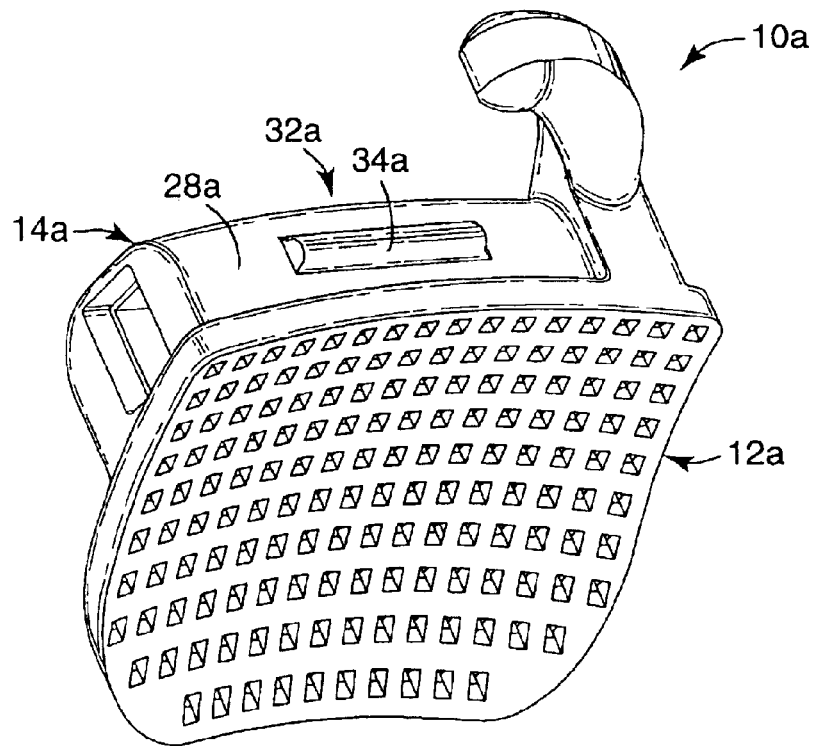
FIG. 4 is a perspective view of the appliance shown in FIG. 3, except that the view in FIG. 4 is taken in a direction looking toward the gingival, mesial and lingual sides of the appliance.

An orthodontic appliance 10a according to another embodiment of the invention is illustrated in FIGS. 3 and 4. Except as mentioned below, the appliance 10a is identical to the appliance 10. As such, a description of the common aspects need not be repeated.

The appliance 10a includes placement enhancement structure 32a that, in this example, comprises elongated ridges 34a that are connected to a body 14a. The ridges 34a each have a longitudinal axis that extends in a mesial-distal direction, although other orientations are also possible. For example, the longitudinal axis of the ridges may extend in buccolabial-lingual directions, or in directions between a mesial-distal reference axis and a buccolabial-lingual reference axis.

The ridges 34a have rounded exterior surfaces that extend in a semicircle when viewed in reference planes perpendicular to the longitudinal axis of an archwire slot 16a, although other shapes are also possible. For example, the cross-sectional shape of the ridges 34a in reference planes perpendicular to the longitudinal axis of the archwire slot may be a triangle, square, rectangle or other polygon.

The placement enhancement structure 32a in this embodiment includes two ridges 34a that are located within a recess 36a. The recess 36a is formed on an occlusal side 24a of the body 14a. The placement enhancement structure 32a also includes a single ridge 34a that is located on a gingival side 28a of the body 14a.

The appliances 10, 10a as exemplified in the drawings are buccal tube appliances that are especially adapted for use with molar teeth. However, the principles of the present invention may be used with other orthodontic appliances as well. For example, orthodontic brackets adapted for bonding to anterior, cuspid and bicuspid teeth may also include placement enhancement structure located along either occlusal and gingival sides of the bracket or along mesial and distal ends of the bracket. In instances wherein the placement enhancement structure is provided along occlusal and gingival sides of brackets, the placement enhancement structure is preferably located between tiewings of the bracket.

Other orthodontic appliances are also possible. For example, the placement enhancement structure may be adapted for use with sheaths, buttons, cleats and other orthodontic components that are affixed to the patient's teeth. The appliances may also be lingual appliances adapted for bonding to lingual surfaces of the patient's teeth, instead of the appliances adapted for bonding to buccolabial surfaces of the teeth as shown in the drawings.

A number of other options are also possible and will apparent to those skilled in the art. Accordingly, the invention should not be deemed limited to the specific examples that are described above in detail, but only by a fair scope of the claims that follow along with their equivalents.

What is claimed is:

1. An orthodontic buccal tube appliance comprising:
   a base for bonding the appliance to a tooth;
   a body extending outwardly from the base, the body having an occlusal side and a gingival side;
   an elongated archwire slot extending across the body in a generally mesial-distal direction; and
   placement enhancement structure extending along at least one of the occlusal and gingival sides for facilitating gripping of the appliance, wherein the placement enhancement structure is selected from the group of two or more side-by-side protrusions, two or more side-by-side cavities and cross-hatching, and wherein said at least one of the occlusal and gingival sides lacks a tiewing.

2. An orthodontic appliance according to claim 1 wherein the protrusions comprise one or more elongated ridges.

3. An orthodontic appliance according to claim 1 wherein the protrusions comprise one or more rounded bumps.

4. An orthodontic appliance according to claim 1 wherein the protrusions are selected from the set of ridges, posts, bumps, pins, pyramids, truncated pyramids, cones and truncated cones.

5. An orthodontic appliance according to claim 1 wherein the cavities are selected from the set of pores, grooves and channels.

6. An orthodontic appliance according to claim 1 wherein the placement enhancement structure is located along both of the occlusal and gingival sides, and wherein the placement enhancement structure that extends along the occlusal side is aligned along an occlusal-gingival reference axis with the placement enhancement structure that extends along the gingival side.

7. An orthodontic appliance according to claim 1 wherein the placement enhancement structure is at least partially located in a recess that extends along at least one of the occlusal and gingival sides.

8. An orthodontic buccal tube appliance comprising:
   a base for bonding the appliance to a tooth;
   a body extending outwardly from the base, the body having an occlusal side and a gingival side;
   an elongated archwire slot extending across the body in a generally mesial-distal direction;
   at least one recess extending along at least one of the occlusal and gingival sides; and
   placement enhancement structure located in at least one recess for facilitating gripping of the appliance, wherein the placement enhancement structure is selected from the group of two or more side-by-side protrusions, two or more side-by-side cavities and cross-hatching, and wherein said at least one of the occlusal and gingival sides lacks a tiewing.

9. An orthodontic appliance according to claim 8 wherein the recess has a bottom wall section that extends generally in an occlusal plane.

10. An orthodontic appliance according to claim 8 wherein the recess includes side wall sections that extend in reference planes generally perpendicular to the longitudinal axis of the archwire slot.

11. An orthodontic appliance according to claim 8 wherein the appliance is a buccal tube.

12. An orthodontic appliance according to claim 11 wherein the recess extends along the occlusal side and is generally aligned with the mesial-distal center of the appliance.

13. An orthodontic appliance according to claim 12 wherein the appliance includes a gingival side having placement enhancement structure that is aligned with the recess in a reference plane perpendicular to the longitudinal axis of the archwire slot.

14. An orthodontic appliance according to claim 8 wherein the occlusal side and the gingival side generally extend in reference planes parallel to an occlusal plane.

15. An orthodontic appliance according to claim 8 wherein the protrusions comprise one or more elongated ridges.

16. An orthodontic appliance according to claim 8 wherein the protrusions comprise one or more rounded bumps.

17. An orthodontic appliance according to claim 8 wherein the protrusions are selected from the set of ridges, posts, bumps, pins, pyramids, truncated pyramids, cones and truncated cones.

18. An orthodontic appliance according to claim 8 wherein the cavities are selected from the set of pores, grooves and channels.

* * * * *